(12) United States Patent
Port

(10) Patent No.: US 9,402,924 B2
(45) Date of Patent: Aug. 2, 2016

(54) DIAGNOSTIC COMPOUNDS FOR TARGETING A CHEMOKINE RECEPTORS

(75) Inventor: Marc Port, Deuil la Barre (FR)

(73) Assignee: GUERBET, Villepinte (FR)

( * ) Notice: Subject to any disclaimer, the term of this patent is extended or adjusted under 35 U.S.C. 154(b) by 1792 days.

(21) Appl. No.: 11/663,548

(22) PCT Filed: Sep. 23, 2005

(86) PCT No.: PCT/EP2005/054797
§ 371 (c)(1),
(2), (4) Date: Mar. 23, 2007

(87) PCT Pub. No.: WO2006/032704
PCT Pub. Date: Mar. 30, 2006

(65) Prior Publication Data
US 2009/0202435 A1 Aug. 13, 2009

(30) Foreign Application Priority Data
Sep. 23, 2004 (FR) ..................................... 04 10062

(51) Int. Cl.
| | |
|---|---|
| *A61K 51/04* | (2006.01) |
| *A61K 49/00* | (2006.01) |
| *C07K 7/64* | (2006.01) |
| *A61K 49/18* | (2006.01) |
| *A61K 49/08* | (2006.01) |
| *B82Y 5/00* | (2011.01) |

(52) U.S. Cl.
CPC ............ *A61K 49/1866* (2013.01); *A61K 49/085* (2013.01); *A61K 49/186* (2013.01); *A61K 51/0446* (2013.01); *A61K 51/0455* (2013.01); *A61K 51/0459* (2013.01); *A61K 51/0497* (2013.01); *B82Y 5/00* (2013.01)

(58) Field of Classification Search
CPC ....... A61K 51/04; A61K 49/00; A61K 49/06; C07K 7/64; C07F 19/00
See application file for complete search history.

(56) References Cited

U.S. PATENT DOCUMENTS

| | | | |
|---|---|---|---|
| 6,045,821 A * | 4/2000 | Garrity et al. | 424/450 |
| 6,440,956 B1 * | 8/2002 | Port | 514/186 |
| 6,706,252 B1 | 3/2004 | Ericsson et al. | |
| 2004/0091913 A1 * | 5/2004 | Livingston et al. | 435/6 |
| 2004/0102428 A1 | 5/2004 | Bridger et al. | |
| 2006/0239926 A1 * | 10/2006 | Port et al. | 424/9.363 |

FOREIGN PATENT DOCUMENTS

| | | |
|---|---|---|
| WO | WO-02/27321 A3 | 4/2002 |
| WO | WO-03/106589 A1 | 12/2003 |
| WO | WO-2004/054615 A1 | 7/2004 |

OTHER PUBLICATIONS

Mukai et al., (J Label Compd. Radiophram. 2003;46:S304).*
Liang et al., (Chem Soc Rev. May 10, 2004;33(4):246-66. Epub Mar. 22, 2004.4):246-66. Epub Mar. 22, 2004).*
Liang, et al., Cancer Research, vol. 64, Jun. 15, 2004, pp. 4302-4308.
Tamaura et al., Biochemical and Biophysical Research Communications, vol. 253, No. 3, 1998, pp. 877-882.
Gerlach et al., The Journal of Biological Chemistry, vol. 276, No. 17, Issue of Apr. 27, 2001 pp. 14153-14160.
Dessolin et al., J. Med. Chem., 1999, vol. 42, No. 2, pp. 229-241.
Le Bon et al., Bioconjugate Chem., 2004, vol. 15, No. 2, pp. 413-423.
Ichiyama et al., PNAS, Apr. 1, 2003, vol. 100, No. 7 pp. 4185-4190.
Mukai et al. J. Label Compd. Radiopharm, 2003 vol. 46, S304.

* cited by examiner

*Primary Examiner* — Cherie M Stanfield
(74) *Attorney, Agent, or Firm* — Birch, Stewart, Kolasch & Birch, LLP

(57) ABSTRACT

The present invention relates to a compound comprising, firstly a component for targeting at least one chemokine receptor and, secondly, a detection component capable of being identified by a medical imaging method.

7 Claims, No Drawings

DIAGNOSTIC COMPOUNDS FOR TARGETING A CHEMOKINE RECEPTORS

The Invention relates to diagnostic compounds for targeting chemokine receptors, in particular CXCR4 receptors, and to the use of these compounds in the medical imaging field.

Chemokines are molecules of the cytokine family, which exhibit-properties of activation, in particular of cells of the leukocyte family, involving in particular chemoattractant properties, properties of calcium mobilization through an increase in intracellular calcium, and enzyme release properties (exocytosis). These chemokines are known for their possible role as inflammation mediators. Several chemokines have been described with reference to their structure and to their affinity for one or more receptors and with reference to their biological properties, in a publication by M. Baggiolini et al., (Advances in Immunology (1994), vol. 55, pages 97-179). A publication by T. N. C. Wells et al., (Journal of Leukocyte Biology, vol. 59, January 1996, 53-60) describes the three-dimensional structure of several chemokines and their specific or non-specific receptors. In general, these chemokines are characterized by the presence, in their primary structure, of conserved cysteine residues (1 to 4 residues, in particular), on the basis of which several subfamilies have been distinguished according to the position of the first two cysteines. These families comprise those of the CXC proteins or of the CC proteins. The presence of these cysteine residues induces the formation disulphide bridges.

The determined role of chemokines and of their receptors has been demonstrated in cancerous proliferation due to metastases, in particular of pulmonary carcinomas (Muller et al, Nature 410: 50-6 (2001), WO 99/47518). Malignant cells from primary tumours will colonize other tissues through the bloodstream or lymphatic circulation of chemokines involved in this process. The molecular mechanisms involved in tumour progress and metastasis (mobility, migration, cell proliferation, adhesion of circulating cancer cells to endothelial cells) have not been completely elucidated. The role of CXCR4 receptors has, however, been demonstrated and ligands capable of targeting CXCR4 receptors and thus of inhibiting tumour progression have been described, in particular in document US 2004 0132642.

The invention relates to the targeting of CXCR4 receptors, not for the treatment, but for the diagnosis of a cancerous pathology, and in particular the evaluation of the risks and of the stage of progress of metastases.

Those skilled in the art are aware, for MRI (magnetic resonance imaging) in particular, of a great number of 'nonspecific' contrast products based on linear or macrocyclic chelates of a paramagnetic metal such as gadolinium, in particular DTPA, DTPA BMA, DTPA BOPTA, DO3A, TETA, TRITA, HETA, DOTA-NHS, TETA-NHS, PCTA, DOTA, M4DOTA, M4DO3A, M4DOTMA, MPDO3A, HBED, EHPG, BFCs. However, these compounds nevertheless do not make it possible to specifically recognize a pathological zone, and in particular tumour metastases.

In contrast to a nonspecific product of the prior art (without targeting of a biological marker) the compounds according to the invention are aimed at specifically identifying biological targets (cells, tissues): exhibiting an overexpression of CXCR4 receptors compared to a non-pathological zone. In particular, the compounds according to the invention are intended to target tumour cells expressing CXCR4 receptors, and preferably metastatic cells.

Thus, according to a first aspect, the invention relates to compounds comprising, firstly, a CXCR4-targeting biovector component and, secondly, a detection component (signal entity) capable of being identified by a medical imaging method.

The detection component is typically a contrast agent that can be detected by MRI imagining, X-rays, gamma-ray scintigraphy, a CT scan, ultrasound, PET, optical imaging, CEST imaging, and in particular Lipocest (lipid nanoparticles exposed to CEST imaging).

In the case of MRI, a contrast is obtained through the administration of contrast agents containing paramagnetic or superparamagnetic metals which have an effect on the relaxivity of water protons. In the case of scintigraphy, the contrast is obtained by virtue of the specific location of a radiopharmaceutical compound emitting gamma- or beta-rays.

In the case of PET, the contrast is obtained by virtue of the specific location of a positron-emitting radiopharmaceutical compound.

In the case of optical imaging, organic fluorochromes (FITC, Cys5.5, for example) and quantum dots may typically be used.

In the case of CEST imaging, an appropriate displacement metal (shift metal) is typically used.

For the targeting of CXCR4 receptors, the invention will use appropriate biovectors chosen in particular from antibodies or small molecules such as peptides, sugars or organic molecules.

According to one embodiment, the signal component comprises at least one chelate, it being possible for a large number of chelates to be used.

A linear chelate from the following may in particular be used: EDTA, DTPA diethylenetriaminepentaacetic acid, N-[2-[bis(carboxymethyl)amino]-3-(4-ethoxy-phenyl)propyl]-N-[2-[bis carboxymethyl)amino]ethyl]-L-glycine (EOB-DTPA), N,N-bis-[2-[bis(carboxymethyl)amino]ethyl]-L-glutamic acid (DTPA-GLU), N,N-bis[2-[bis-(carboxymethyl)amino]ethyl]-L-lysine (DTPA-LYS), monoamide or bisamide derivatives of DTPA, such as N,N-bis[2-[carboxymethyl[(methylcarbamoyl)methyl]amino]ethyl] glycine (DTPA-BMA), 4-carboxy-5,8,11 tris (carboxymethyl)-1-phenyl-2-oxa-5,8,11-triazatridecan-13-oic acid (BOPTA).

A macrocyclic chelate from the following may in particular be used; 1,4,7,10-tetraazacyclododecan-1,4,7,10-tetraacetic acid (DOTA), 1,4,7,10-tetra-azacyclododecan-1,4,7-triacetic acid (DO3A), 10-(2-hydroxypropyl)-1,4,7,10-tetra-azacyclododecan-1,4,7-triacetic acid (HPDO3A), 2-methyl-1,4,7,10-tetra-azacyclododecan-1,4,7,10-tetraacetic acid (MCTA), (alpha, alpha', alpha", alpha'")-tetramethyl-1,4,7,10-tetraazacyclododecan-1,4,7,10-tetraacetic acid (DOTMA), 3,6,9,15-tetraazabicyclo[9.3.1]pentadeca-1(15), 11,13-triene-3,6,9-triacetic acid (PCTA), NOTA.

Use may also be made of derivatives in which one or more carboxylic groups are in the form of a corresponding salt, ester, or amide; or a corresponding compound in which one or more carboxylic groups are replaced with a phosphonic and/ or phosphinic group, such as 4-carboxy-5,11-bis(carboxymethyl)-1-phenyl-12-[(phenyl-methoxy)methyl]-8-(phosphonomethyl)-2-oxa-5,8,11-triazatridecan-13-oic acid, N,N'-[(phosphonomethylimino)di-2,1-ethanediyl]bis[N-(carboxymethyl)glycine], N,N'-[(phosphonomethylimino) di-2,1-ethanediyl]bis[N-(phosphonomethyl)glycine], N,N'-[(phosphinomethylimino)di-2,1-ethanediyl]bis[N-(carboxymethyl)glycine], 1,4,7,10-tetraazacyclododecane-1,4,7,10-tetrakis[methylene(methylphosphonic)] acid, or 1,4,7,10-tetraazacyclododecane-1,4,7,10-tetrakis[methylene (methylphosphinic)] acid.

A chelate from the following may also be used: DOTA gadofluorines, DO3A, HPDO3A, TETA, TRITA, HETA, DOTA-NHS, M4DOTA, M4DO3A, PCTA and their 2-benzyl-DOTA derivatives, alpha-(2-phenethyl)-4,7,10-tetraazacyclododecane-1-acetic-4,7,10-tris(methylacetic) acid, 2-benzylcyclohexyldiethylenetriaminepentaacetic acid, 2-benzyl-6-methyl-DTPA, 6,6"-bis[N,N,N",N"-tetra(carboxymethyl)aminomethyl-4'-(3-amino-4-methoxyphenyl)-2,2',6',2"-terpyridine, N,N'-bis(pyridoxal-5-phosphate)-ethylenediamine-N,N'-diacetic acid (DPDP) and ethylenedinitrilotetrakis(methyl-phosphonic) acid (EDTP).

More broadly, the chelate(s) forming the signal entity may correspond to the formula of document WO01/60416.

The coupling of chelates with biovectors is known in the prior art, and generally involves a chemical linker as described in document WO01/60416. The structure and the chemical nature of the linker are defined so as to allow chemical coupling between the biovector and the chelate(s) used.

In the case of MRI, the relaxivity of these chelates in T1 imagining is typically of the order of 4 to 20 mMol$^{-1}$.G$^{-1}$.s$^{-1}$. It is recalled that the longitudinal relaxivity $r_1$ of a paramagnetic contrast product gives the measure of its magnetic efficiency and makes it possible to assess its influence on the signal recorded. In MRI medical imaging, the contrast products modify the proton relaxation time, and the increase in relaxivity obtained makes it possible to obtain a higher signal. The chelates are chosen so as to form stable complexes with ions of a paramagnetic metal of atomic number 21-29, 42-44 or 58-70, in particular Gd(III), Dy(III), Fe(III), Mn(III) and Mn(III), and Tm III for CEST imaging.

In the case of scintigraphy, the metal is a radionuclide, in particular $^{99}$Tc, $^{117}$Sn, $^{111}$In, $^{97}$Ru, $^{67}$Ga, $^{68}$Ga, $^{89}$Zr, $^{177}$Lu, $^{47}$Sc, $^{105}$Rh; $^{188}$Re, $^{60}$Cu, $^{62}$Cu, $^{64}$Cu, $^{67}$Cu, $^{90}$Y, $^{159}$Gd, $^{149}$Pr or $^{166}$Ho. According to one implementation, the metal is a radionucleide for PET imaging.

According to another embodiment, the signal component is of the SPIO or USPIO superparamagnetic nanoparticle type. Preferably, the particle is a particle of iron oxide or hydroxide, in particular of magnetite ($Fe_3O_4$), maghemite ($\gamma$-$Fe_2O_3$), or other transition atoms. The size is less than 100-15.0 nm, preferably with a hydrodynamic diameter of between 5 and 60 nm.

According to another embodiment, the signal component is of the nanoparticulate emulsion type, possibly containing perfluorocarbons, such as particles described in document WO 03/062198, U.S. Pat. No. 5,958,371, U.S. Pat. No. 5,080,885 or U.S. Pat. No. 6,403,056. The nanoparticles in emulsion are typically coupled to a large number of chelates, for example 10000 to 100 000 DTPA per particle. Various perfluorocarbon emulsions are recalled in document U.S. Pat. No. 6,676,963 (perfluorodecaline, perfluorooctane, perfluorodichlorooctane, perfluoro-n-octyl bromide, perfluoroheptane, perfluorodecane, perfluorocyclohexane, perfluoromorpholine, perfluorotripropylamine, perfluorotributyl-amine, perfluorodimethylcyclohexane, perfluorotrimethylcyclohexane, perfluoro-dicyclohexyl ether, perfluoro-n-butyltetrahydrofuran). Use may be made of lipids/surfactants intended to form an outer coating of the nanoparticles for coupling of the CXCR4-targeting ligands, comprising in particular phospholipids, fatty acids, cholesterol, or other derivatives, where appropriate conjugated to PEGs. Various techniques can be used for covalently coupling the CXCR4-targeting component, and optionally other organic molecules, including the chelates mentioned above, to the compounds of the outer coating, for example with the formation of amides or of sulphide links.

More broadly, the CXCR4-targeting biovectors can be grafted or encapsulated in an appropriate transport system for biological recognition which is diagnostically effective. Such systems may be liposomes, micelles, vesicles, microgels, multilayer lipid particles, polymers of saccharides and/or of ethylene oxide.

The invention relates to the use of a composition according to the present invention, for the diagnosis of a pathology associated with an overexpression or an underexpression of chemokine receptors.

The invention also relates to the use of the compounds described above, for the diagnosis of diseases associated with an overexpression or an underexpression of CXCR4 compared to a normal tissue, preferably the diagnosis of tumours, in particular the detection of tumour metastases.

The invention also relates to the use of the compounds described above, for the preparation of a diagnostic composition for use in the diagnosis of diseases associated with an overexpression or an underexpression of CXCR4 compared with a normal tissue, preferably the diagnosis of tumours, in particular tumour metastases.

Examples of administration of compositions for medical imaging are described in the prior art, for example in document WO 0226776. The diagnostic agent is administered in sufficient amount for satisfactory imaging. In MRI, a dose of metal ion of from 0.02 to 1.5 mmol/kg of bodyweight will, for example, be used.

Pharmaceutically and physiologically acceptable carriers that make if possible to form diagnosis compositions (contrast products) comprising the compounds described above are known from the prior art. Salts (sodium, calcium, meglumine), pH-modifiers (acetic acid, citric acid, fumaric acid) and antioxidants will, for example, be used.

According to a preferred implementation, the biovector is a bicyclam, such as the compound AMD3100 that can be directly biocoupled, or one of its derivatives described in: Bioconjugate Chem, 2004, 15, 413-423; The American Society for Biochemistry and Molecular Biology, 2003, vol 278, No. 47, 47136-47144; J. Med. Chem., 1999 42, 229-241; Chemical Reviews, 2003, vol 103, no. 9.

Compounds capable of targeting CXCR4 receptors, chosen from the following compounds, will be in particular be chosen:

According to another implementation, the biovector is a CXCR4-targeting peptide such as the synthetic peptide TN14003 described in Cancer Research, 64, 4302-4308, 15 Jun. 2004.

Use may also be made of the non-peptide compound KRH-1636 described in PNAS, April 2003, vol 100, no. 7, 4185-4190, or antibodies capable of targeting CXCR4 receptors, or compounds described in U.S. Pat. No. 6,667,320, US 2004/0157818 (Yanaka et al), US 2004/0134642 (USA government), US 2004/0102428, US 2004/0037825 (Bond et al), US 2004/0019058, US 2003/0220482 (vMIP-II), US 2003/0091569 (Gerritsen et al), US 2002/0039993 (SDF1), US 2002/0077339' (Bridger et al), 2004/0009171 (Genentech).

In a more overall respect, the inventors have studied the use, for MRI for inflammatory or cancerous processes of compounds of which the biovector is capable of specifically targeting receptors of chemokines other than CXCR4 receptors. The biovector may in particular be a chemokine or an agonist or antagonist or a derivative of chemokines of the CC, CXC. CX3C, C families. According to one implementation, for example, the biovector is an antagonist of the SDF-1 chemokine (stroma cell derived factor 1), such as those described in The EMBO journal, vol 16, no. 23, 6996-7007, 1997 or CTCE-9908, or, in general, peptidomimetic or truncated structures of SDF-1.

The chemokines IL-8, MCP-1 and MIP-1 in particular are useful in the context of the invention. In addition, the expression of several chemokine receptors, including the CXCR3, CCR7 and CCR10 receptors, has been demonstrated in melanoma cells, as has the expression of CXCR1 and CXCR2 receptors for colon carcinoma.

The coupling with the biovector is carried out in an appropriate manner, typically using a chemical linker. The bismacrocyclic compounds (AMD 3100 and the like) can be conjugated to fluorescent, paramagnetic or radioactive labels. For this, it is possible to use one of the secondary amine functions of the nitrogenous rings, the other amine functions being protected with a suitable group introduced beforehand during the synthesis of the heterocycles. These groups are chosen from appropriate protective groups for amine functions, such as amides, carbamates. The macrocyclic compound can then be linked to the label by the free secondary amine function by means of a peptide coupling reaction, typically by condensation with an isocyanate, by reaction on a squaric acid ester, by alkylation. It is also possible to introduce, between the heterocyclic nitrogen and the label, a cross-linker that makes it possible to distance the two active parts of the molecule from one another. These cross-linkers are obtained by reaction of heterobifunctional units of variable size and chemical nature, such as polymethylene chains, oligoethylene glycols, an amino acid, a peptide or an aromatic ring. These heterobifunctional linkers have a function that is reactive with the secondary amine function at one of their ends, such as a carboxylic acid function optionally activated in the form of an ester, an alkyl halide, or a squaric acid ester; and another reactive function-available at the other end, for receiving the label. Among the possible functions, mention may be made of the amine function, the carboxylic acid function, a thiol, a maleimide group or a squaric acid ester. Examples of heterobifunctional cross-linkers may be found in Bioconjugate Techniques-Greg. T. Hermanson-Academic Press-1996-p 228-286. When the conjugation of the two active entities is carried out, the blocked functions are deprotected according to the appropriate chemical protocols (see Protective Groups in Organic Synthesis-second edition—T. W. Green, P.G.M. Wuts-JOHN WILEY SONS-1991 and Protecting Groups-3rd edition-P. J. Kocienski-THIEME-2004).

The applicant has in particular studied the following products.

The tert-butyl ester of 11-{4-[4,8-bis-tert-butoxycarbonyl-11-(4-carboxybutyl)-1,4,8,11-tetraazacyclotetradec-1-ylmethyl]benzyl}-1,4,8,11-tetraazacyclotetradecane-1,4,8-tricarboxylic acid of formula (Boc-AMD-(CH$_2$)$_4$COOH):

Formula I

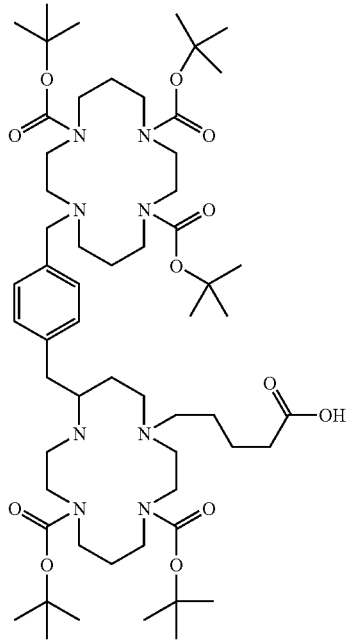

was prepared according to the data in the literature (Bioconjugate Chemistry, vol. 15, no. 2, 2004)

The following examples are given by way of non-limiting indication.

EXAMPLE 1

Stage 1: Coupling

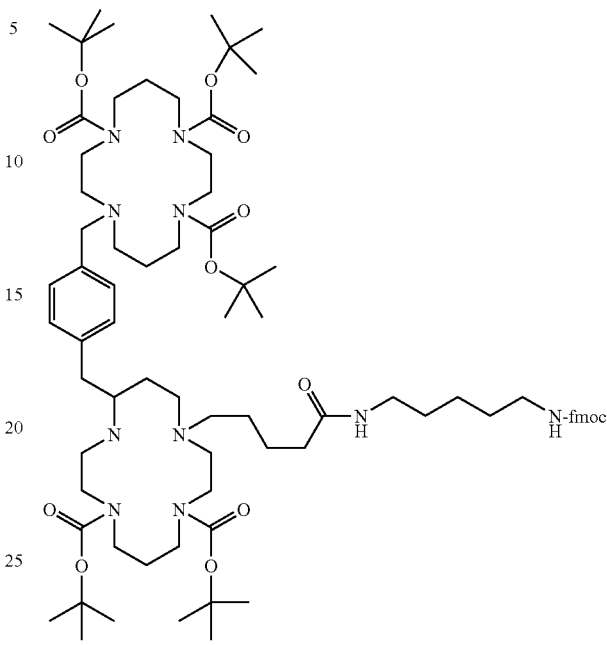

44 mg of coupling agent BOP (benzotriazol-1-yloxytris (dimethylamino)phosphonium hexafluorophosphate) are added to a solution of 36 mg of the amine mono-Fmoc-1,5-diaminopentane (in hydrochloride form, Novabiochem®), 100 mg of the acid Boc-AMD-(CH$_2$)$_4$COOH (0.09 mmol) and 32 mg of triethylamine in 5 ml of dichloromethane. The solution is stirred at ambient temperature for 4 h and then washed successively with a solution of 5% NaHCO$_3$, 5% KHSO$_4$ and, finally, with water. The organic phase is dried over Na$_2$SO$_4$ and evaporated to dryness. The product is purified on silica get (elution CH$_2$Cl$_2$/MeOH). m/z: ES+ 1600.

Stage 2: Deprotection of the Fmoc

Formula II

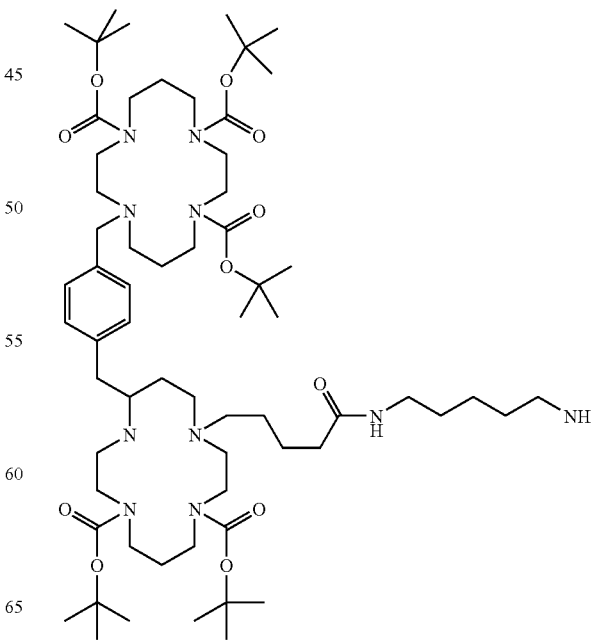

The compound obtained in stage 1 is dissolved in a solution of piperidine in DMF (20%). The solution is stirred at ambient temperature for 3 h and then evaporated under a strong vacuum. The oil obtained is washed with petroleum ether and then chromatographed on silica gel (CH$_2$Cl$_2$/MeOH). m/z: ES+ 1189

EXAMPLE 2

Stage 1: 5 (1,3-Dioxo-1,3-dihydroisoindol-2-yl)-2-(1,4,7,10-tetraazacyclo-dodec-1-yl)pentanoic acid benzyl ester

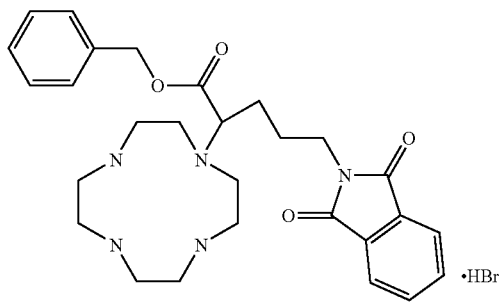 [SMILES: O=C(OCc1ccccc1)C(CCCN1C(=O)c2ccccc2C1=O)N1CCNCCNCCNCC1 ; Br]

55 g of cyclen base (320 mmol) are dissolved in 550 ml of CH$_3$CN, to which are added, dropwise, 119.8 g of brominated derivative (2-bromo-5-(1,3-dioxo-1,3-dihydrolso-indol-2-yl)pentanoic acid benzyl ester, 288 mmol) dissolved in 550 ml of CH$_3$CN. The medium is stirred at ambient temperature overnight. The precipitate is filtered off and washed thoroughly with acetonitrile. 138 g of product are obtained in the form of a powder.

TLC: CH$_2$Cl$_2$/MeOH/NH$_4$OH at 25% (80/40/3).
Visualization UV and CuSO$_4$, Rf: 0.3.

Stage 2: 5-(1,3-Dioxo-1,3-dihydroisoindol-2-yl)-2-(4,7,10-trisethoxycarbonyl-methyl-1,4,7,10-tetraaza-cyclododec-1-yl)pentanoic acid benzyl ester

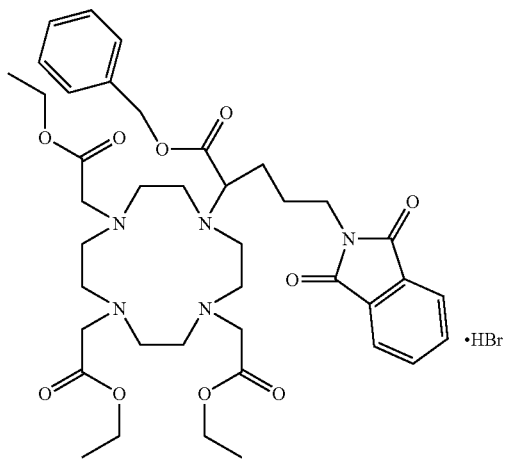 [SMILES: CCOC(=O)CN1CCN(CC(=O)OCC)CCN(C(CCCN2C(=O)c3ccccc3C2=O)C(=O)OCc2ccccc2)CCN(CC(=O)OCC)CC1 ; Br]

60 g of the compound obtained in stage 1 (102 mmol) and 50.1 g of Na$_2$CO$_3$ (464 mmol) are added to a solution of 59.1 g of ethyl bromoacetate (Aldrich®, 358 mmol) in CH$_3$CN (1.1 l). The reaction medium is heated at 80° C. overnight with a covering of argon. After elimination of the precipitate, the filtrate is concentrated and washed thoroughly with CH$_3$CN. The product is crystallized from CH$_3$CN by dropwise addition of Et$_2$O. 89.8 g of product are obtained in the form of a white solid. TLC: CH$_2$Cl$_2$/MeOH (9/1). Visualization UV and KMnO$_4$.
Rf: 0.4

Stage 3: 5-Amino-2-(4,7,10-triscarboxymethyl-1,4,7,10-tetraazacyclododec-1-yl)pentanoic acid

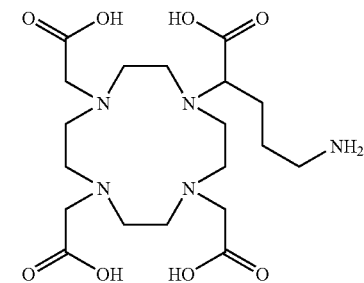 [SMILES: NCCCC(C(=O)O)N1CCN(CC(=O)O)CCN(CC(=O)O)CCN(CC(=O)O)CC1]

A solution of 54 g of compound obtained in stage 2 (64 mmol) in 37% hydrochloric acid (1.8 l) is refluxed overnight in a 5-liter reactor. After cooling and filtration, the filtrate is concentrated and purified on silanized silica (elution with water). After evaporation under reduced pressure, the product is washed with ether. 45 g of product are obtained in the form of a white solid. The product is desalified by passage over OH resin. 30 g of product are isolated in the form of white crystals. HPLC: Hypercarb® 5µ, 200×4.6, 250 Å.
Solvent A: 0.037N sulphuric acid; solvent B: CH$_3$CN; UV detection at 201 nm; Tr: 18 min.

Stage 4: 5-Amino-2-(4,7,10-triscarboxymethyl-1,4,7,10-tetraazacyclododec-1-yl)pentanoic acid gadolinium complex

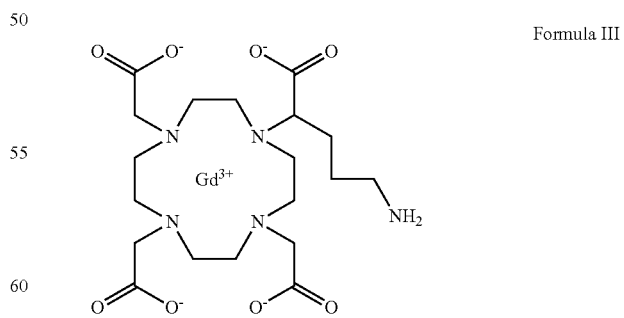

Formula III 7.2 g of the compound obtained in stage 3 (16 mmol) are dissolved in 70 ml of water and the pH is adjusted to 5.5 by adding 6N hydrochloric acid. 2.9 g of Gd$_2$O$_3$ (8 mmol) are added and the reaction medium is heated to 80°. The pH of the solution increases regularly and must be maintained at between 5.2 and 5.7 by means of the dropwise addition of 6N hydrochloric acid. After two hours, the pH stabilizes at 5.7. The slight cloudiness is filtered off over a Whatman® filter and the filtrate is concentrated. 11.1 g of product are obtained in the form of white flakes. HPLC: Hypercarb® 5μ, 200×4.6, 250 A. Solvent A: 0.037N sulphuric acid, solvent B: $CH_3CN$. UV detection at 201 nm. Tr: 1.0 min.

Stage 5: 5-(2-Ethoxy-3,4-dioxocyclobut-1-eny-lamino)-2-(4,7,10-tris-carboxymethyl-1,4,7,10-tetraazacyclododec-1-yl)pentanoic acid gadolinium complex

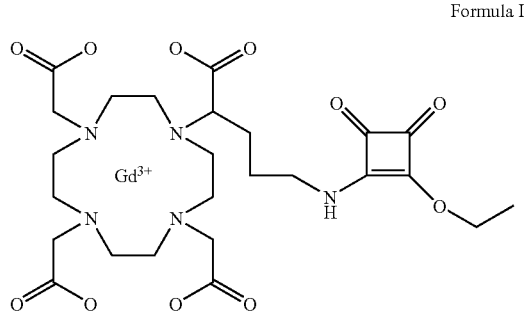

Formula IV 8 g Of compound obtained in stage 4 are dried by azeotropic distillation with toluene, and then suspended in 90 ml of anhydrous DMSO under a covering of argon. 2.8 ml of sieve-dried $Et_3N$ (1.7 eq.) and 5 g of diethyl squarate (Aldrich®, 2.5 eq.) are subsequently added. The medium is stirred at ambient temperature under a covering of argon for 1 hour. The mixture is precipitated from 600 ml of ether. The solid obtained is filtered off, and then washed with dichloromethane. After filtration and drying, 7.5 g of a white solid (81.5% yield) are recovered. HPLC: symmetry C18. 5μ, 250×46, 100 Å. A: water TFA, pH=2.7. B: $CH_3CN$. Detection at 201 and 254 nm. Tr: 19.8 min.

EXAMPLE 3

Stage 1: Coupling

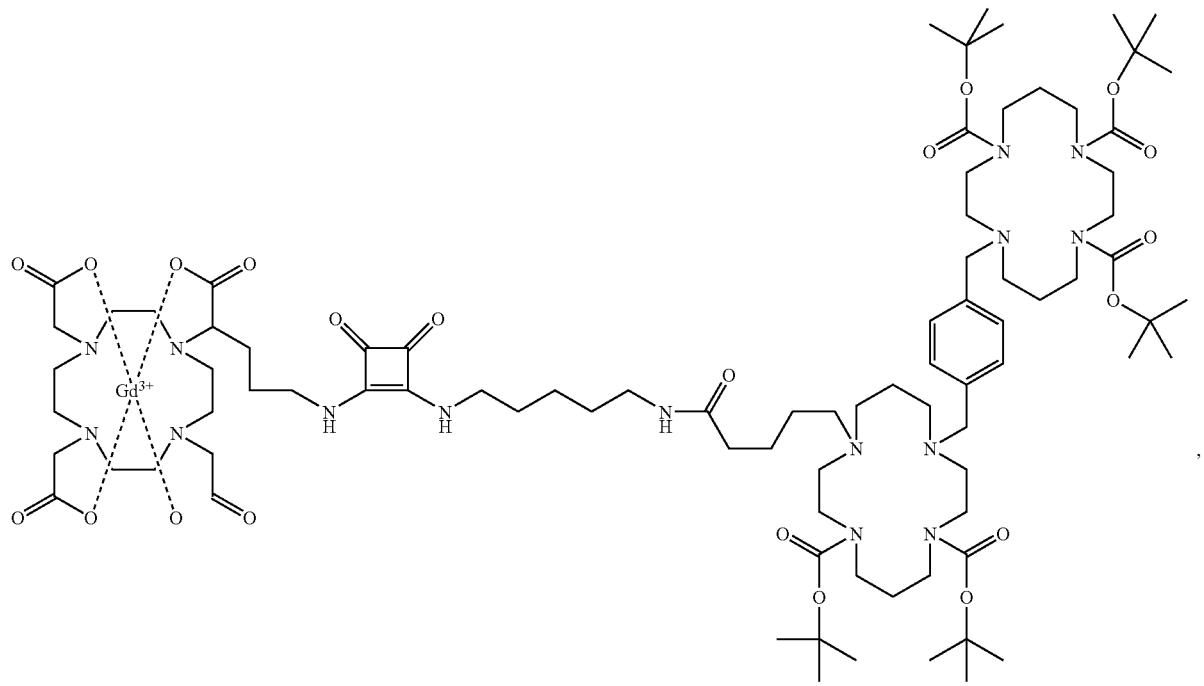

The compound obtained in stage 5 of Example 2 (100 mg, $1.35 \times 10^{-4}$ mol) is dissolved in 10 ml of aqueous $Na_2CO_3$ solution, pH 9.4. The compound obtained in stage 2 of Example 1 (176 mg) is introduced while maintaining the pH at 9.4 by adding $Na_2CO_3$. A few drops of DMF are added until dissolution is complete. After reaction at ambient temperature for 48 h, the medium is precipitated from an ethanol/ethyl ether mixture. The precipitate is filtered off and then dried. m/z: ES+ 1882.

Stage 2: Deprotection of the Tert-Butyls

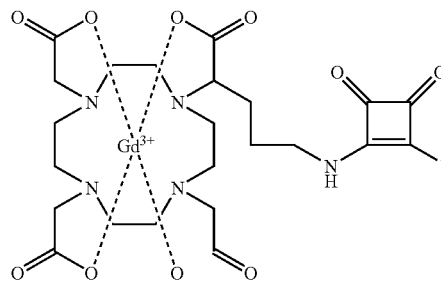
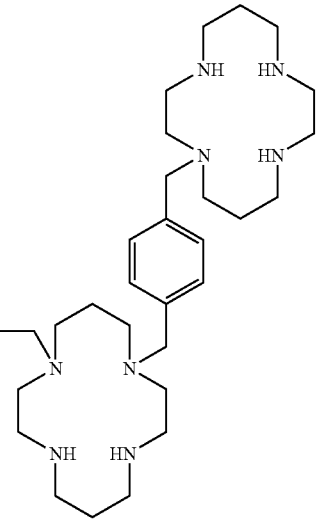

The compound obtained in stage 1 is dissolved in a mixture of 10 cm³ of TFA/TIS/H₂O in 90/5/5 proportions. The medium is stirred at ambient temperature for 5 h and the solvent is then evaporated off under reduced pressure. The residue is taken up in ethyl ether and the precipitate is filtered and then dried. The product is subsequently purified by a preparative HPLC on a Symmetry® column with an eluent consisting of water/TFA PH 3/CH₃CN. m/z: ES+ 1381

EXAMPLE 4

Stage 1: Coupling

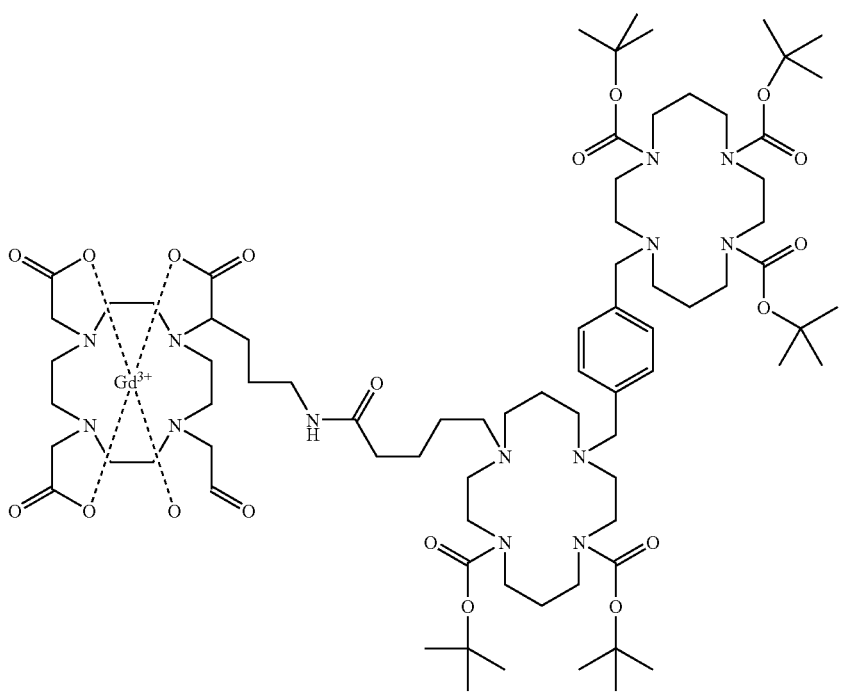

0.1 g of the complex prepared in stage 4 of Example 2, and 197 mg (i.e. 1.1 eq.) of Boc-AMD-$(CH_2)_4$COOH are dissolved in 25 ml of water/DMF. 405 mg of EDCl (i.e. 1.3 eq.) and 0.01 g of HOBt are added. The reaction medium is heated at 40° C. for 12 hours and the pH is maintained at approximately 6 by adding a few drops of 2N NaOH. Purification: The reaction medium is precipitated from 250 ml of acetone. The product is filtered and the white solid obtained is dried over $P_2O_6$.

MS: ES+, M/Z=1702 with z=1

Stage 2: Deprotection

CH$_3$CN; the reaction mixture is then stirred at 80° C. for 20 h and then cooled to ambient temperature and filtered and the solvent is evaporated off. The residuals taken up with 500 ml of a 1N aqueous solution of HCl in the presence of one volume of diethyl ether. After separation of the organic phase, the aqueous phase is neutralized with NaHCO$_3$ and then extracted with CH$_2$Cl$_2$. After washing with water and then drying over magnesium sulphate, the organic phase is concentrated and the residue is purified on a silica column (Merck® 500 g, d=10 cm), elution being carried out with CH$_3$COOC$_2$H$_5$. m=20.9 g; m/z: ES+ 544.6.

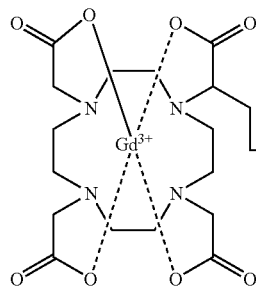

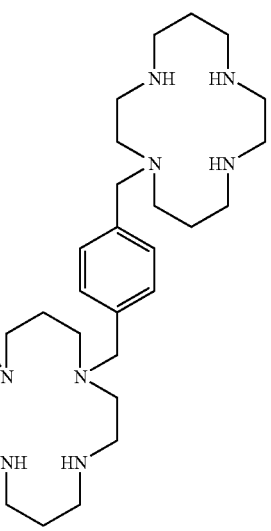

According to the protocol of stage 2 of Example 3, starting with the compound obtained in stage 1. MS: ES+, M/Z=1202 with z=1

EXAMPLE 5

Stage 1: (13-Bromo-6,9-bisethoxycarbonylmethyl-3,6,9,15-tetraaza-bicyclo[9.3.1]pentadeca-1(14),11(15), 12-trien-3-yl)acetic acid methyl ester

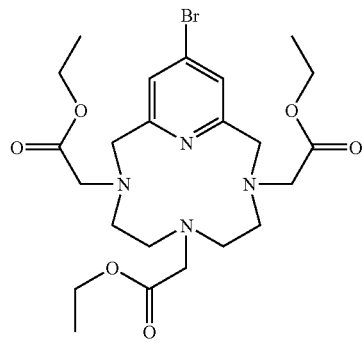 [SMILES: CCOC(=O)CN1CCN(CC(=O)OCC)Cc2cc(Br)cc(n2)CN(CC(=O)OCC)CC1]

22 g of 13-bromo-3,6,9,15-tetraazabicyclo[9.3.1]pentadeca-1(15),11,13-triene, obtained according to J. Heterocyclic Chem. 27, 1990, pages 167-169, are introduced into 440 ml of CH$_3$CN in the presence of 48 g of calcinated K$_2$CO$_3$ and the mixture is maintained at 80° C. for 1 h before the addition of a solution of 50 g of ethyl bromoacetate in 100 ml of Stage 2: [13-(3-tert-Butoxycarbonylaminopropenyl)-6,9-bisethoxycarbonyl-methyl-3,6,9,15-tetraazabicyclo[9.3.1]pentadeca-1(14),11(15),12-trien-3-yl]acetic acid ethyl ester

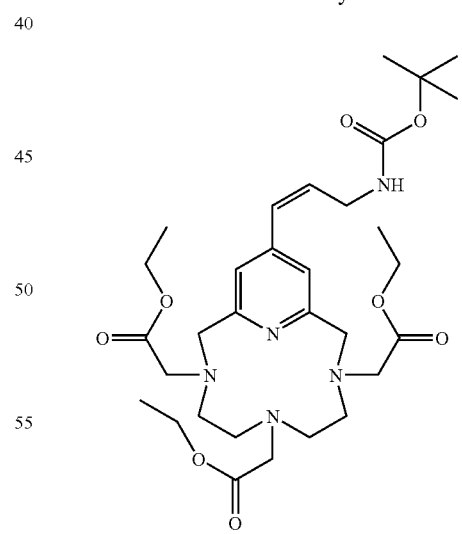

6 g of 3-(tert-butyloxycarbonylamino)propene, 10 ml of triethylamine, then 800 mg of triphenylphosphine and, finally, 400 mg of palladium acetate are added to a solution of 5 g of the compound obtained in stage a) dissolved in 100 ml of toluene. After heating at 80° C. overnight under an inert atmosphere, the medium is evaporated off and the residue is taken up with an aqueous solution of hydrochloric acid (pH=1). The aqueous phase is. Washed with 1 volume of diethyl ether and then of toluene before being brought to pH 6 through the addition of NaOH (1N).

After extraction of the aqueous solution with CH$_2$Cl$_2$, the organic phase dried over magnesium sulphate is evaporated off. A brown oil is obtained, which is chromatographed on silica gel. m=2.8 g. m/z: ES+ 621.

Stage 3: [13-(3-tert-Butoxycarbonylaminopropyl)-6, 9-bisethoxacarbonylmethyl-3,6,9,15-tetraazabicyclo [9.3.1 pentadeca-1(14),11(15),12-trien-3-yl]-acetic acid ethyl ester

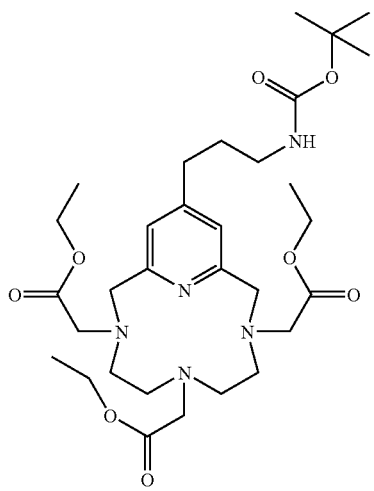 [SMILES: CCOC(=O)CN1CCN(CC(=O)OCC)Cc2cc(CCCNC(=O)OC(C)(C)C)cc(n2)CN(CC(=O)OCC)CC1]

200 mg of catalyst palladium-on-charcoal at 10% are added to 2 g of the compound obtained in stage b) dissolved in 80 ml of CH$_3$OH, and the reaction mixture is then stirred for 2 h 30 at 20° C. under 4×10$^5$ Pa of hydrogen. Ater filtration over Clarcel®, the solvent is evaporated off and 1.8 g of oil are obtained after silica gel chromatography. m/z: ES+ 623.

Stage 4: [13-(3-tert-Butoxycarbonylaminopropyl)-6, 9-biscarboxymethyl-3,6,9,15-tetraazabicyclo[9.3.1] pentadeca-1(14),11(15),12-trien-3-yl]acetic acid

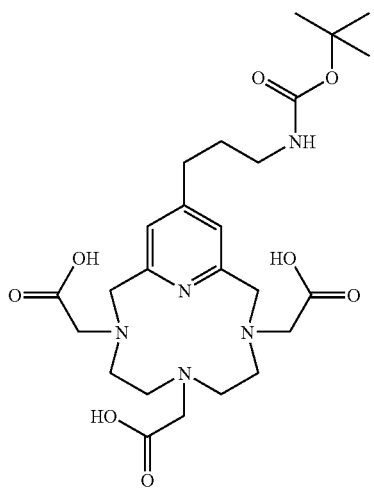 [SMILES: CC(C)(C)OC(=O)NCCCc1cc2nc(c1)CN(CC(=O)O)CCN(CC(=O)O)CCN(CC(=O)O)C2]

1 g of the compound obtained in stage 3) dissolved in 20 ml of a 5N aqueous solution of NaOH and 20 ml of CH$_3$OH are heated at 70° C. for 18 h. After concentration of the reaction medium, the residue is taken in water and the solution, brought to pH 5.5-6 with a few drops of acetic acid. Is concentrated before being purified by chromatography on a column (d=15 cm) containing 50 g of silanized silica (Merck® 0.063-0.200 μm), elution being carried out with water. After concentration to dryness, 480 mg of white crystals are obtained. m/z: ES− 536.5.

Stage 5: [13-(3-tert-Butoxycarbonylaminopropyl)-6, 9-biscarboxymethyl-3,6,9,15-tetraazabicyclo[9.3.1] pentadeca-1(14),11(15),12-trien-3-yl]acetic acid gadolinium complex

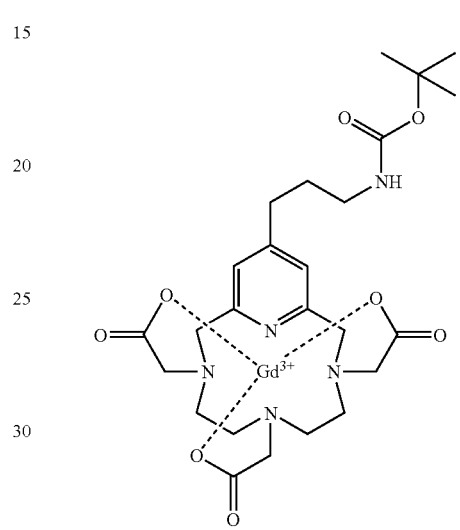

300 mg of the compound obtained in stage d) are dissolved in 10 ml of water and then 100 mg of Gd$_2$O$_3$ are added all at once and the mixture is heated at 60° C. for 3 h 45 min maintaining the pH of between 5.5 and 6 by adding a 1N aqueous solution of NaOH. After filtration, the reaction medium is evaporated off and the residue is crystallized from ethanol. After treatment with a Chelex® 100 resin (Bio-Rad), 320 mg of white crystals are obtained. m/z: ES− 691.

Stage 6: [13-(3-Aminopropyl)-6,9-biscarboxymethyl-3,6,9,15-tetra-azabicyclo[9.3.1]pentadeca-1 (14),11(15),12-trien-3-yl]acetic acid gadolinium complex

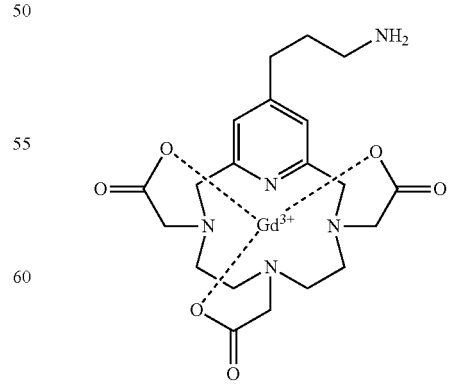

A solution, of 300 mg of the complex obtained in stage e) in 18 ml of CF$_3$COOH is maintained at 25° C. for 3 h with stirring, before eliminating the liquid under reduced pressure. The residue is taken up in diethyl ether and the suspension is filtered. After elimination of the solvent, the residue is introduced portionwise into a suspension of at least 1 ml of weak anionic resin (OH⁻) in 5 ml of water; at the end of the addition, the pH, which is stable must be between 8 and 8.5. The resin is then separated by filtration, the solvent is eliminated and the residue is precipitated by addition of ethyl ether m=200 mg. m/z: ES+ 593.

EXAMPLE 6

Stage 1: Coupling

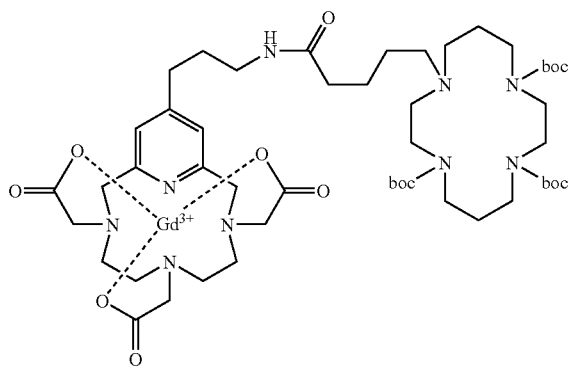

According to the protocol of stage 1 of Example 4, starting with 100 mg of the gadolinium complex prepared in stage 6 of Example 5 and 102 mg of 11-(4-carboxy-butyl)-1,4,8,11-tetraazacyclotetradecane-1,4,8-tricarboxylic acid tert-butyl ester prepared according to the data in the literature (J. of Medicinal chemistry, 1999, vol 42, no. 2, p229-241). m/z: ES+ 1176.

Stage 2: Deprotection

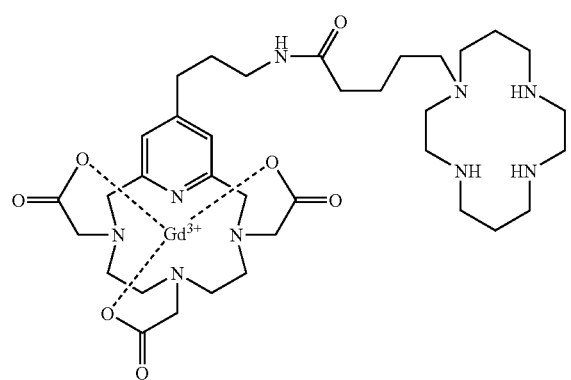

According to the protocol of stage 2 of Example 4, starting with the compound obtained in stage 1. m/z: ES+ 875.

EXAMPLE 7

Stage 1: Coupling

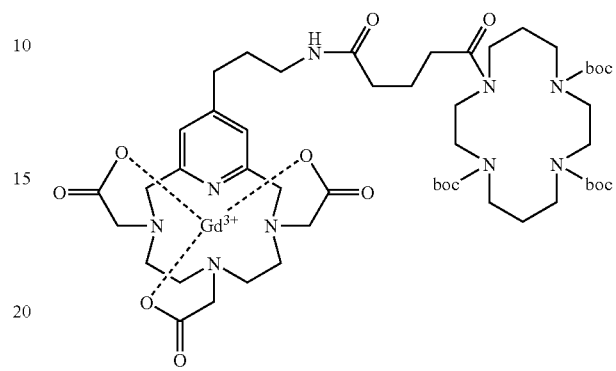

According to the protocol of stage 1 of Example 4, starting with 100 mg of the gadolinium complex prepared in stage 6 of Example 5 and 104 mg of 11-(4-carboxy-butyryl)-1,4,8,11-tetraazacyclotetradecane-1,4,8-tricarboxylic acid tert-butyl ester prepared according to the data in the literature (J. of Medicinal chemistry, 1999, vol 42, no. 2, p 229-241). m/z: ES+ 1190.

Stage 2: Deprotection

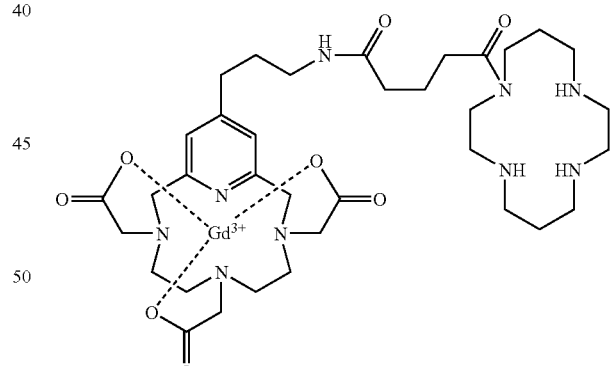

According to the protocol of stage 2 of Example 4, starting with the compound obtained in stage 1.

m/z: ES+ 889.

EXAMPLE 8

Coupling of the compound obtained in stage 2 of Example 1 with the bimetal complexes described in patent WO 2004/112839.

example no. 3, pages 93-94 and 91 to 93, of formula VI:
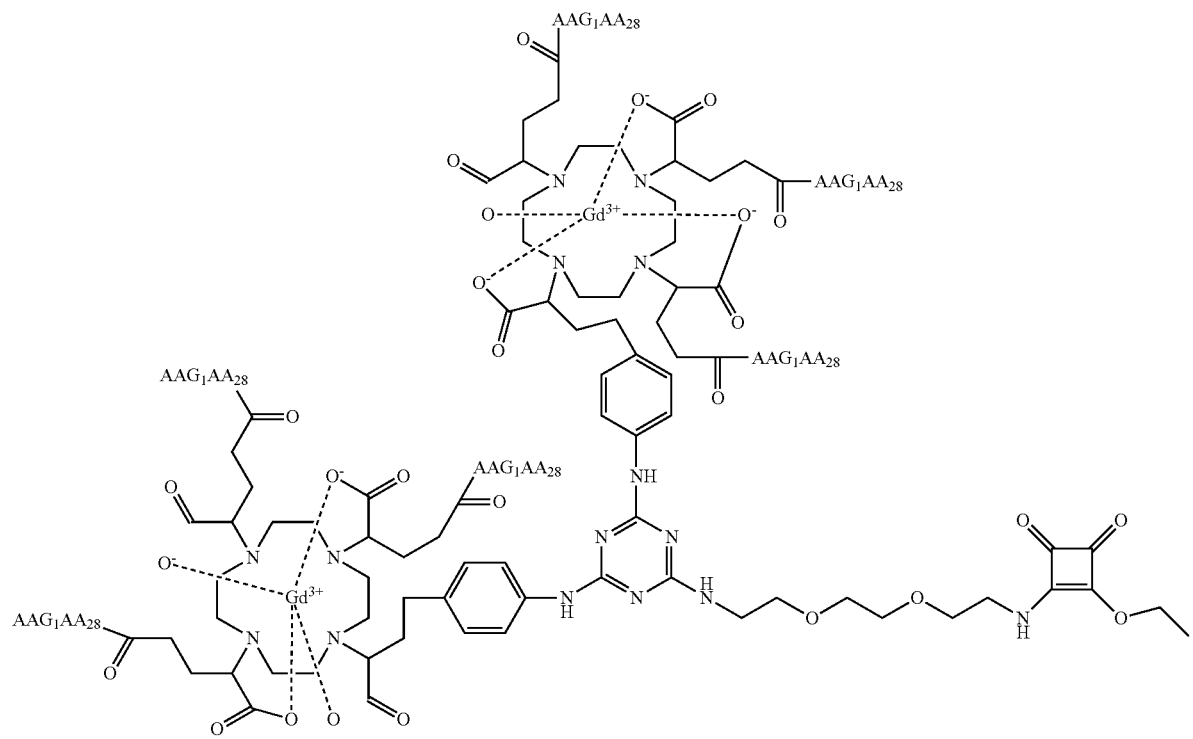
example 6, p 98 to 101, and 96 to 98 of formula VII:
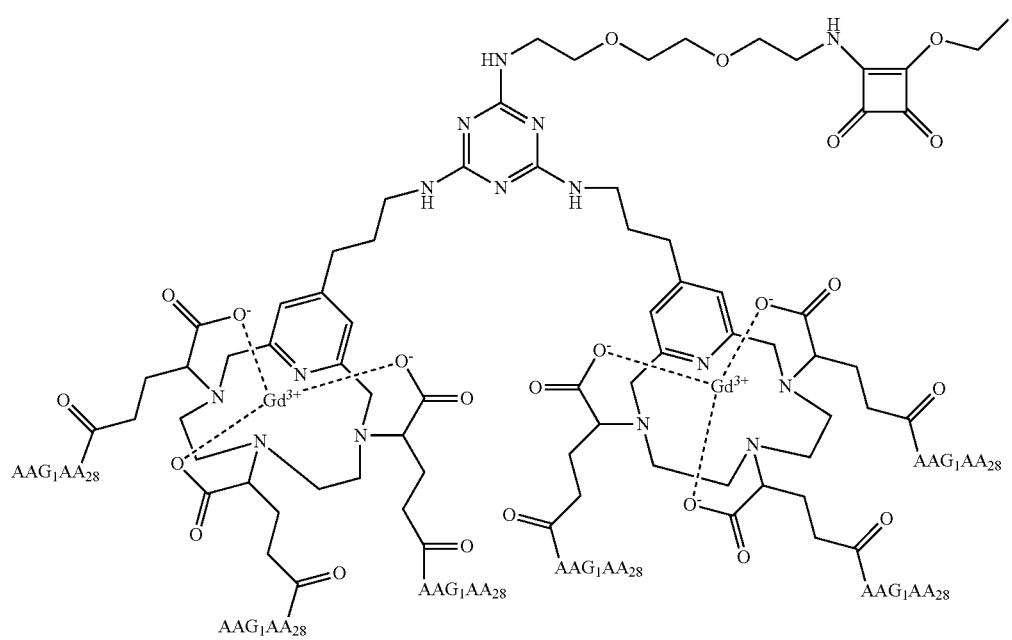

with AAG1AA28=

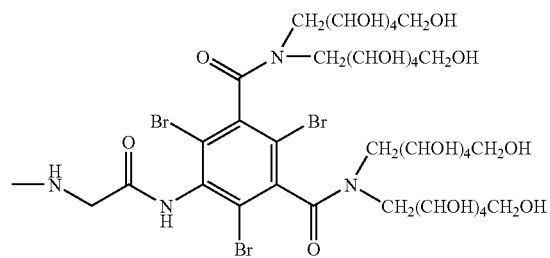

Stage 1: Coupling

| Compound | Mol. weight | Amount involved | Number of mol. |
|---|---|---|---|
| Formula VI | 8802.59 | 300 mg | $3.41\ 10^{-5}$ |
| Formula II | 1187.67 | 47.5 mg | $4\ 10^{-5}$ |

| Compound | Mol. weight | Amount involved | Number of mol. |
|---|---|---|---|
| Formula VII | 8632.43 | 300 mg | $3.48\ 10^{-5}$ |
| Formula II | 1187.67 | 50 mg | $4.18\ 10^{-5}$ |

300 mg of a previously described bimetallic compound (formula VI or VII) are dissolved in 2 ml of water. The pH is brought to 9.5 by adding $Na_2CO_3$. 1.2 equivalents of the compound described in stage 2 of Example 1 (formula II) are added. The reaction medium is stirred at ambient temperature for 3 days and is precipitated from ethanol.

Stage 2: Deprotection

The compound obtained according to stage 1 is dissolved in 10 ml of the mixture trifluoroacetic/water/triisopropylsilane (90/5/5). After 4 h at ambient temperature with stirring, the TFA is eliminated by evaporation under vacuum. The reaction medium is precipitated from ether. The product obtained by filtration is subsequently purified by preparative HPLC. HPLC: Superpher Select B® column; water-TFA pH 3/$CH_3CN$

| Compound | Mol. Weight | Amount obtained | M/Z ES +. |
|---|---|---|---|
| VIII | 9443.61 | 110 mg | 9445 |
| IX | 9273.44 | 90 mg | 9276 |

Formula VIII

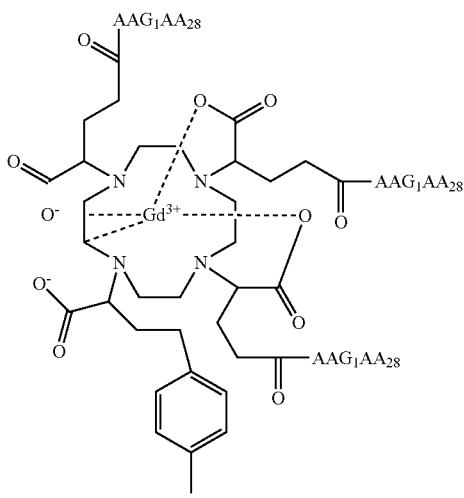

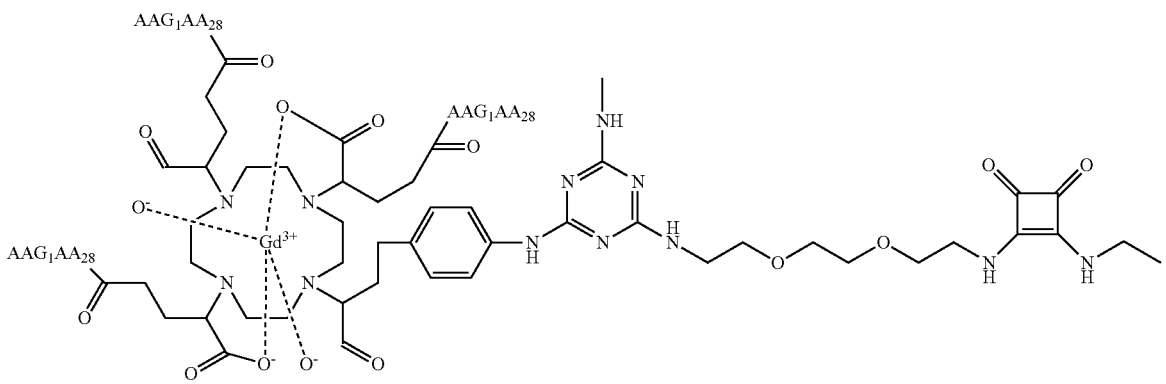

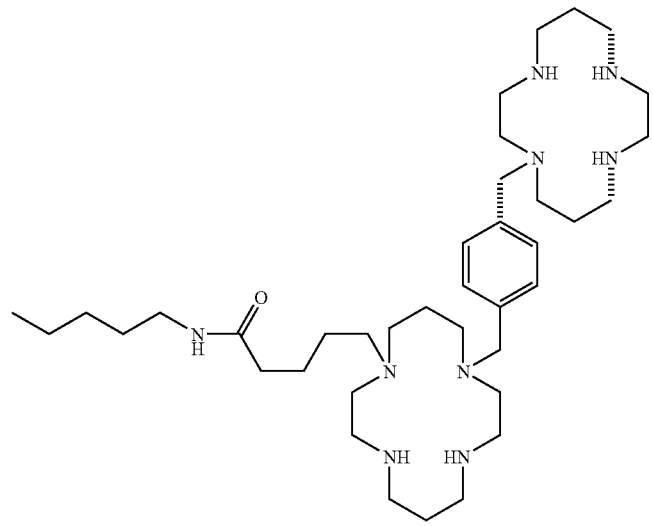
Formula IX
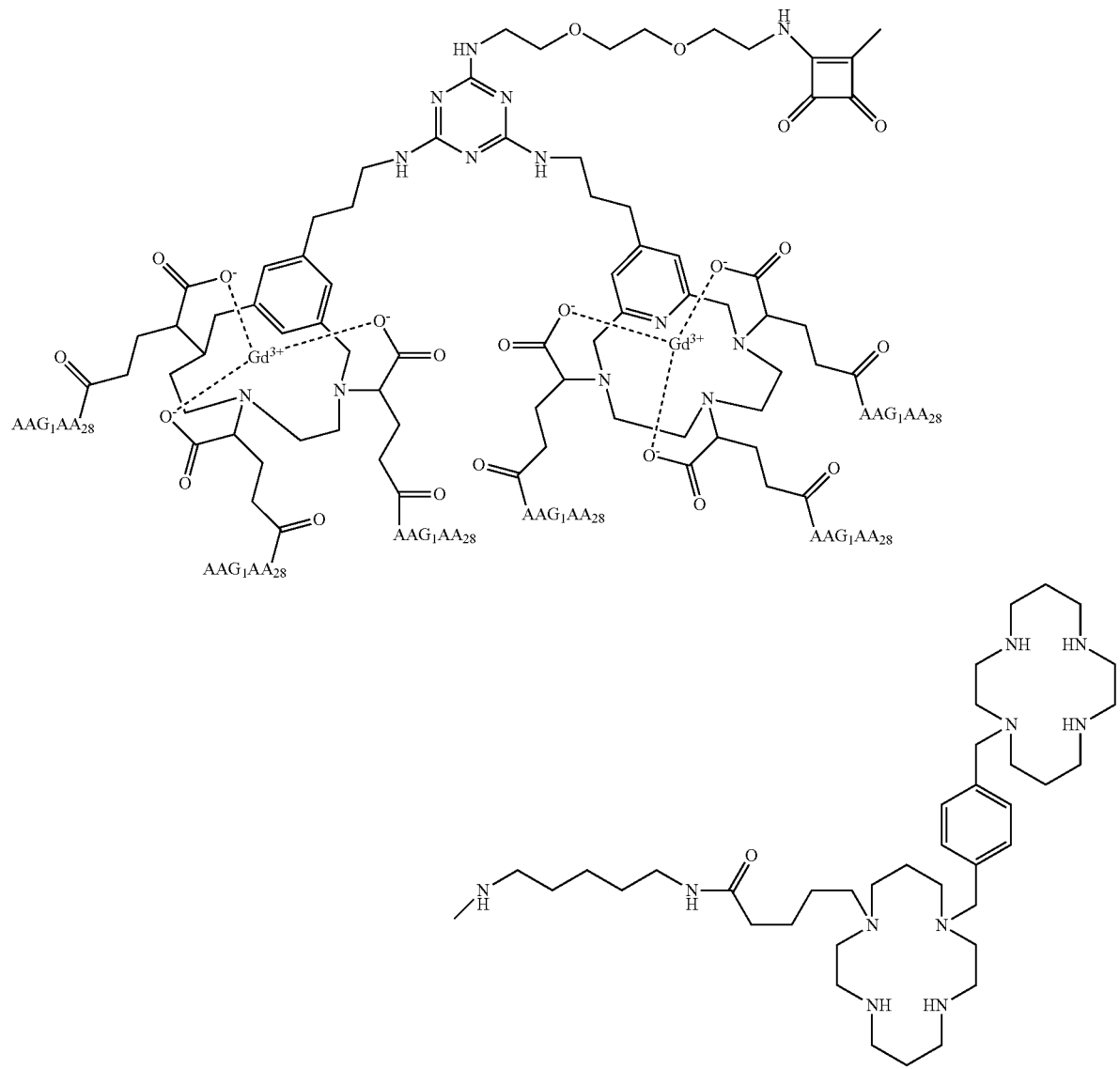

EXAMPLE 9

Synthesis of Cyclopeptides of Formula X

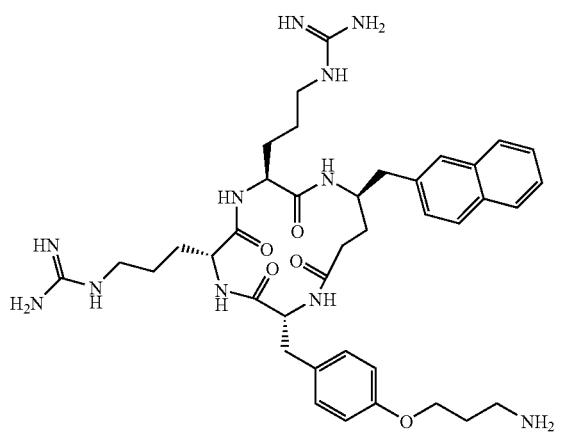

Formula X

The peptide was prepared according to the method described in J. of Medicinal Chemistry, 2005, vol. 48, no. 9, p 3280-3289. The solid-phase synthesis was carried out on chlorotrityl resin using amino acids protected with the Fmoc group.

The tyrosine used in the original publication was replaced with a substituted analogue of formula:

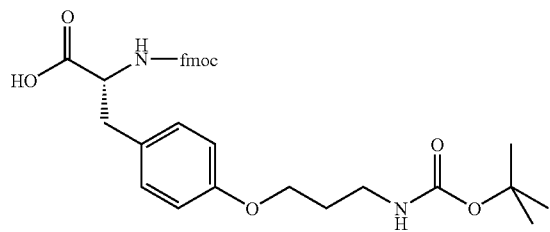

This compound was prepared according to the method described in Tetrahedron Letters vol. 36, No 35, p 6193-6196, 1995.

EXAMPLE 10

Coupling of the Cyclopeptide of Formula X onto Nanoparticles of Fe Oxide

The nanoparticles were prepared according to the methods described in patent WO 2004/058 275 (US 2004/253181), Examples 8 and 9 for the preparation of the colloidal solutions of magnetic particles and Example 10 to 12 for the complexation of the magnetic particles with a gem-bisphosphonate coating of Example 1 of WO 2004/058275.

The coupling is carried out in a manner similar to that described for Examples 13 to 15 of WO 2004/058275. A solution of 100 mg of peptide of formula X and 110 mg of EDCl (1-(3-dimethylaminopropyl)-3-ethylcarbodiimide chlorohydrate) are added gradually maintaining the pH at around 7, to 50 cm³ of iron oxide nanoparticle solution. The pH of the solution is brought back to 6.5 with NaOH (0.1N). The solution is stirred and then filtered over a membrane with a porosity of 0.22 μm (STERICUP Millipore®). The solution is then ultrafiltered over a 30 KD membrane. [Fe] 0.250 M/L.
PCS size=28 nm
Degree of grafting [compound A/Fe]=1.65% mol/mol
Degree of grafting [peptide/compound A]=31%

EXAMPLE 11

Coupling of the amine R—NH2, N,N'-[bis(2,3,4,5,6-pentahydroxyhexyl)]-2,4,6-tribromo-5-(glycylamino)isophthamide of formula:

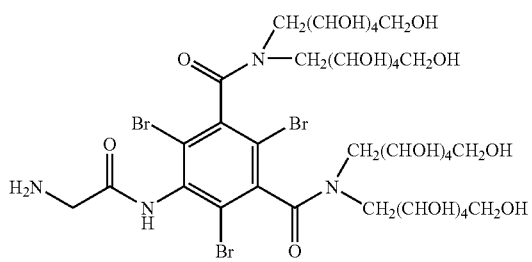

can be prepared according to the protocol described in patent: EP 0 922 700 A1.

A solution consisting of 2.5 g of amine R—NH₂ in 10 cm³ of water is added to 50 cm³ of solution obtained in Example 10' at ambient temperature. The pH is adjusted to 7 by adding 0.1M NaOH. 1 g of EDCl is added and the solution is stirred at ambient temperature for 3 h. The pH is adjusted to 7 and the mixture is stirred at ambient temperature overnight. After filtration over a membrane with a porosity of 0.22 μm, the solution is ultrafiltered over a membrane with a cut-off threshold of 30 KD.
[Fe]=0.228 M/L PCS size=28.3 nm
Degree of grafting [compound A/Fe]=1.62% mol/mol
Degree of grafting [peptide/compound A]=32%
Degree of grafting [R—NH₂/compound A]=62%

EXAMPLE 12

Coupling of Amino PEG 750 (O-(2-Aminoethyl)-O'-Methyl Polyethylene Glycol 750 FLUKA®)

A solution consisting of 2 g of amino PEG 750 in 10 cm³ of water is added to 50 cm³ of solution obtained in Example 10, at ambient temperature. The pH is adjusted to 7 by adding 0.1M NaOH. The 1 g of EDCl is added and the solution is stirred at ambient temperature for 3 h. The pH is adjusted to 7 and the mixture is stirred at ambient temperature overnight. After filtration over a membrane with a porosity of 0.22 μm, the solution is ultrafiltered over a membrane with a cut-off threshold of 30 KD.
[Fe]=0.212 M/L PCS size 27.8 nm
Degree of grafting [compound A/Fe]=1.70% mol/mol
Degree of grafting [peptide/compound A]=30%
Degree of grafting [R—NH₂/compound A]=62%

The applicant has developed the following biological protocols for measuring the effectiveness of the products.

Affinity/specificity in vitro for CXCR-4: biological ASSAY No. 1: binding assay based on recognition, by the vectorized signal entity, of a cell expressing the target protein (HL-60). The recognition specificity is evaluated by virtue of competition experiments that show that an excess of free vector has a direct inhibitory role on the binding of the prototype tested. The specificity is also validated by comparison with assays obtained with the non-vectorized reference molecule. The cell target chosen is the human promyeloid cell HL-60 described in the literature as being strongly positive for CXCR4 [R. Möhle et al.: "The chemokine receptor CXCR-4 is expressed on CD34+ hematopoietic progenitor and leukemic cells and mediates transendothelial migration induced by stromal cell-derived factor-1" Blood 12: 4523-4530 (1998)].

Model for Binding of HL-60 Cells:
Cell: HL-60
Times: Incubation time in the presence of the test product: time points range from 0.5 h to 4 h at 37° C.
Controls: Verification of the level of CXCR-4 expression of the HL-60 by flow cytometry.
  Incubation of the cells in the presence of the non-vectorized reference molecule.
Specificity: Inhibition of the binding of the prototypes with an excess of free vector or comparison with the results obtained with the non-vectorized reference molecule.
Results: Amounts of Fe or of Gd present in the cell pellets after assaying by ICP-AES or ICP-MS, respectively (amounts related to a million cells or to mg of proteins).
  The analysis of the results takes into account the amount of Fe or of Gd found with the vectorized particles, related to that detected:
  1/ in the presence of the non-vectorized contrastophore
  2/ in the presence of the vectorized prototype and of an excess of ligand (×100).
  These results make it possible to determine the influence of the vector on the recognition mechanism, and the recognition specificity is studied by means of the competition experiments with excess free vector.

Affinity/specificity in vitro for CXCR-4: Biological ASSAY No. 2: binding assay based on recognition, by the vectorized signal entity, of a call expressing the target protein with, as control, the same cell, but negative for the receptor. The recognition specificity is evaluated by virtue of experiments comparing the results obtained on positive cells with those obtained on negative cells. The cell target chosen is the CHO (Chinese Hamster Ovary) cell, which is negative for CXCR-4 expression.

Model of Binding/Internalization on CHO Cells:
Cells: CHO positive and negative for the human CXCR4 receptor
Time periods: Incubation time in the presence of the test product: time points ranging from 0.5 h to 2 h at 37° C.
Controls: Incubation of the cells in the presence of the non-vectorized reference molecule.
Specificity: Comparison with the various groups (positive and negative CHO cells/vectorized product and reference product).

The invention claimed is:

1. A molecule comprising, firstly, a CXCR4-receptor-targeting component which is non-complexed AMD3100, and, secondly, a detection component capable of being identified by a medical imaging method, in which the detection component is at least one linear or macrocyclic chelate of an ion of a paramagnetic metal or of a radionucleide or a shift metal,
  wherein the chelate is selected from the group consisting of DTPA, DTPA BMA, DTPA BOPTA, DO3A, TETA, TRITA, HETA, DOTA, NOTA and PCTA.

2. The molecule of claim 1 in which the chelate is PCTA.

3. A diagnostic composition comprising the molecule according to claim 1 and a pharmaceutically acceptable carrier.

4. Method for the diagnosis of a pathology associated with an overexpression or an underexpression of CXCR4 receptors, comprising the administration of an effective amount of a molecule according to claim 1 to a patient in need thereof.

5. Method for the diagnosis of a pathology associated with an overexpression or an underexpression of CXCR4 receptors, comprising the administration of an effective amount of a composition according to claim 3 to a patient in need thereof.

6. The method of claim 5 in which the pathology is tumour.

7. The method of claim 5 in which the pathology is tumour metastases.

* * * * *